(12) United States Patent
Rosenthal

(10) Patent No.: US 9,925,176 B2
(45) Date of Patent: *Mar. 27, 2018

(54) SODIUM CHANNEL BLOCKER DELIVERY SYSTEM WITH SCLERAL LENS

(71) Applicant: Boston Foundation for Sight, Needham, MA (US)

(72) Inventor: Perry Rosenthal, Newton, MA (US)

(73) Assignee: Boston Foundation for Sight, Needham, MA (US)

( * ) Notice: Subject to any disclaimer, the term of this patent is extended or adjusted under 35 U.S.C. 154(b) by 111 days.

This patent is subject to a terminal disclaimer.

(21) Appl. No.: 14/611,421

(22) Filed: Feb. 2, 2015

(65) Prior Publication Data
US 2015/0148899 A1 May 28, 2015

Related U.S. Application Data

(63) Continuation of application No. 14/167,255, filed on Jan. 29, 2014, now Pat. No. 8,945,603, which is a continuation of application No. 12/878,287, filed on Sep. 9, 2010, now Pat. No. 8,673,340.

(60) Provisional application No. 61/243,037, filed on Sep. 16, 2009, provisional application No. 61/241,090, filed on Sep. 10, 2009.

(51) Int. Cl.
| | |
|---|---|
| *A61F 2/14* | (2006.01) |
| *A61K 31/165* | (2006.01) |
| *A61K 31/445* | (2006.01) |
| *A61K 9/00* | (2006.01) |
| *A61K 31/135* | (2006.01) |
| *A61K 31/4164* | (2006.01) |
| *A61K 47/20* | (2006.01) |
| *A61K 47/30* | (2006.01) |
| *G02C 7/04* | (2006.01) |

(52) U.S. Cl.
CPC ............ *A61K 31/445* (2013.01); *A61F 2/145* (2013.01); *A61K 9/0048* (2013.01); *A61K 31/135* (2013.01); *A61K 31/165* (2013.01); *A61K 31/4164* (2013.01); *A61K 47/20* (2013.01); *A61K 47/30* (2013.01); *G02C 7/04* (2013.01)

(58) Field of Classification Search
CPC .............. A61K 31/135; A61K 31/165; A61K 31/4164; A61K 31/445
See application file for complete search history.

(56) References Cited

U.S. PATENT DOCUMENTS

| | | | |
|---|---|---|---|
| 5,452,031 A | 9/1995 | Ducharme | |
| 5,760,077 A * | 6/1998 | Shahinian, Jr. | ...... A61K 31/167 514/540 |
| 7,591,566 B2 | 9/2009 | Galke et al. | |
| 7,695,135 B1 | 4/2010 | Rosenthal | |
| 8,673,340 B2 * | 3/2014 | Rosenthal | ............ A61K 31/135 351/159.01 |
| 8,945,603 B2 * | 2/2015 | Rosenthal | ............ A61K 31/135 351/159.01 |
| 2002/0161013 A1 | 10/2002 | Liu et al. | |
| 2003/0158147 A1 | 8/2003 | Yerxa et al. | |
| 2006/0290883 A1 * | 12/2006 | Rosenthal | ................ G02C 7/04 351/159.12 |
| 2007/0042969 A1 | 2/2007 | Rauschkolb-Loffler et al. | |
| 2007/0112318 A1 | 5/2007 | Leahy et al. | |
| 2008/0107713 A1 | 5/2008 | Orilla et al. | |
| 2008/0206332 A1 | 8/2008 | Kidney et al. | |
| 2012/0220603 A1 * | 8/2012 | Pajouhesh | ............ C07D 211/34 514/254.04 |
| 2013/0178477 A1 * | 7/2013 | Zhang | ................ A61K 31/4985 514/249 |

OTHER PUBLICATIONS

Rosenthal et al. (American Journal of Ophthalmology, vol. 130, No. 1, 33-41, Published Jul. 2000).*
Beyreuther et al., "Lacosamide: A Review of Preclinical Properties," CNS Drug Reviews, vol. 13, pp. 21-42 (2007).
Errington et al., "The Investigational Anticonvulsant lacosamide selectively enhances slow inactivation of voltage-gated Sodium Channels," Mol. Pharmacol. 73(1):157-69 (2008).
European Medicines Agency, "Withdrawal Assessment Report for Lacosamide Pain UCB Pharma. International Nonproprietary Name: lacosamide. Procedure No. EMEA/H/C/894", Pre Authorization Evaluation of Medicines for Human Use. London, UK. Dec. 5, 2008. 16 pages.
Gerald Hecht, *Chapter 43: Ophthalmic Preparations*, in Remington: The Science and Practice of Pharmacy, 821-835 (A.R. Gennaro, ed., 20th edition, Lippincott Williams & Wilkins, Philadelphia, PA, 2000).
International Search Report and Written Opinion dated Nov. 29, 2010 for International patent Application No. PCT/US10/48260 filed Sep. 9, 2010.
Logan et al., "Plain Bupivacaine: an unpredictable spinal anaesthetic agent," Br. J. Anaesth., vol. 58, pp. 292-296 (1986).
Mahé et al., "Efficacy and safety of three ophthalmic inserts for topical anaesthesia of the comes. An exploratory comparative dose-ranging, double-blind, randomized trial in healthy voluteers," Br. J. Clin. Pharmacol. 59(2):200-226 (2005).
Risco and Millar, "Ultratructural Alterations in the Endothelium in a Patient with Topical Anesthetic abuse keratopathy," Ophthalmology 99(4):628-633 (1992).
Shahinian et al., "dilute Topical Proparacaine for pain relief after photorefractive keratectomy," Ophthalmology 104(8):1327-1332 (1991).

(Continued)

*Primary Examiner* — Alma Pipic
(74) *Attorney, Agent, or Firm* — Wilmer Cutler Pickering Hale and Dorr LLP

(57) ABSTRACT

A scleral lens is provided with a sodium channel blocker or a sodium channel modulator disposed in the pre-corneal tear film between the scleral lens and the cornea. This system can be used to deliver sodium channel blockers or a sodium channel modulators not currently used because of poor bioavailability. Methods of using this sodium channel blocker delivery system or a sodium channel modulator delivery system are also disclosed.

20 Claims, 2 Drawing Sheets

(56) References Cited

OTHER PUBLICATIONS

Sheets et al., "Differential block of Sensory neuronal voltage-gated sodium channels by lacosamide [(2R)-2-(Acetylamino)-N-benzyl-3-methoxypropanamide], lidocaine, and Carbamazepine," The Journal of Pharmacology and experimental therapeutics, vol. 326, pp. 89-99 (2008).

Varga et al., "Topical Anesthetic Abuse Ring Keratitis," Cornea 16(4):424-429 (1997).

Yoos et al., "Spinal 2-Chloroprocaine: A comparison with Small-Dose bupivacaine in volunteers," Anesth Analg, vol. 100, pp. 566-572 (2005).

\* cited by examiner

SODIUM CHANNEL BLOCKER DELIVERY SYSTEM WITH SCLERAL LENS

CROSS REFERENCE TO RELATED APPLICATIONS

This application is a continuation of U.S. patent application Ser. No. 14/167,255, filed Jan. 29, 2014, which is a continuation of U.S. patent application Ser. No. 12/878,287, filed Sep. 9, 2010, now U.S. Pat. No. 8,673,340, which claims the benefit of priority to U.S. Provisional Application Ser. No. 61/241,090, filed Sep. 10, 2009, and U.S. Provisional Application Ser. No. 61/243,037, filed Sep. 16, 2009, the disclosures of each of which are incorporated herein by reference in their entirety.

TECHNICAL FIELD

This disclosure relates generally to a delivery system for retaining a sodium channel blocker at the surface of an eye when a scleral lens is disposed on the eye; a method of using a scleral lens to retain a sodium channel blocker at the surface of the eye; and methods for treating conditions and diseases of the eye.

BACKGROUND

Eye diseases and conditions can be treated with topical agents, such as drops or ointments, which use direct absorption to reach therapeutic drug levels at the target tissue. Topical application is especially useful for the cornea, which has virtually no blood supply and is easily accessible for topical application. When drugs are applied topically in the form of drops or ointment to the cornea, however, the drug solution rapidly disperses into the tear film and flows into the tear drainage system, thereby reducing bioavailability. Non-limiting examples of factors affecting the bioavailability of a drug (i.e., drug levels) in the cornea and to the anterior chamber of the eye include the duration of the drug's effective concentration at the surface of the cornea, and the drug's ability to be absorbed into the corneal tissue.

Delivering medications in the form of eye drops can have two main disadvantages. First, the concentration of the drug can rapidly fall below therapeutic levels, potentially requiring frequent applications of the drug. Second, high concentrations of the drug may be necessary to achieve adequate penetration into the eye because of the drug's brief contact time with the eye, and these high concentrations may be toxic.

An existing method of delivering a drug to the cornea involves dehydrating a soft contact lens, then soaking the lens in a solution of the drug. This method provides an initial burst release of the drug followed by continuous decline in the amount of drug at the cornea. This leads to limited bioavailability of the drug after the initial burst release.

Another method of delivering a drug to the cornea involves soaking a collagen shield in a solution of the drug. These collagen shields are opaque and must be worn in a recess under the lids. Because the impregnated drug is carried to the corneal surface by the tears, its bioavailability is limited in dry eye disease, a common condition in eyes with neuropathic pain.

SUMMARY

A scleral lens rests on the sclera of the eye without substantially touching the cornea. A scleral lens defines a "fluid compartment" between the inner surface of the vaulted area and the cornea. This fluid compartment is also referred to as a fluid reservoir, a pre-corneal tear film, an expanded pre-corneal tear film, or as a supplemented pre-corneal tear film.

The scleral lens also provides a novel method of retaining a drug at the corneal surface in the expanded pre-corneal tear film, which is retained at the surface of the cornea by the scleral lens. The drug is disposed on the back of the scleral lens. The drug may be added to the fluid compartment of the scleral lens, which is then inserted into the eye. Alternatively, the drug is administered to the eye, then the scleral lens is inserted into the eye.

A scleral lens provides high bioavailability of drugs to the relatively avascular cornea, and perhaps to the anterior chamber of the eye, without the potential risks of systemic spillover or the requirement of frequent administration. The scleral lens retains the drug at the cornea, and thus can better maintain a controlled concentration of the drug at the site of administration compared to other known methods. This approach can require less frequent dosing regimens, which reduces noncompliance. This also enables the use of low, non-toxic concentrations of drug to be applied to the eye. The scleral lens provides these benefits while keeping the cornea oxygenated and allowing the patient to see, or even enhancing the patient's vision.

In one aspect, the present disclosure relates to a sodium channel blocker delivery system including a scleral lens to be disposed on an eye of a patient, wherein the scleral lens includes an optic portion having a first curvature, and a scleral portion having a second curvature, wherein the first curvature is adapted to cover a cornea of the eye without substantially touching the cornea; the second curvature is adapted to contact a sclera of the eye without substantially touching the cornea; and the optic portion and the scleral portion intersect to form an angle less than 180 degrees measured from the anterior side of the scleral lens, and a sodium channel blocker disposed on the posterior side of the lens.

In another aspect, the present disclosure relates to a method of treating corneal neuropathic pain in the eye of a patient, where the method includes administering a sub-anesthetic concentration of a sodium channel blocker or a sodium channel modulator to the eye; and applying a scleral lens to the eye, where the scleral lens includes an optic portion having a first curvature, and a scleral portion having a second curvature, wherein the first curvature is adapted to cover a cornea of the eye without substantially touching the cornea; the second curvature is adapted to contact a sclera of the eye without substantially touching the cornea; and the optic portion and the scleral portion intersect to form an angle less than 180 degrees measured from the anterior side of the scleral lens.

In another aspect, the present disclosure relates to a method of retaining a sodium channel blocker or a sodium channel modulator at the surface of the eye of a patient, where the method includes administering a sub-anesthetic concentration of the sodium channel blocker or the sodium channel modulator to the eye; and applying a scleral lens to the eye, where the scleral lens includes an optic portion having a first curvature, and a scleral portion having a second curvature, wherein the first curvature is adapted to cover a cornea of the eye without substantially touching the cornea; the second curvature is adapted to contact a sclera of the eye without substantially touching the cornea; and the optic portion and the scleral portion intersect to form an angle less than 180 degrees measured from the anterior side of the scleral lens.

In some embodiments, the sodium channel blocker is a sodium channel blocker anesthetic, tricyclic antidepressant or antiepileptic. In other embodiments, the sodium channel blocker is selected from the group consisting of bupivacaine, lidocaine, proparacaine, tetracaine, ropivacaine, levobupivacaine, and amitriptyline. In some embodiments, the sodium channel blocker is in a solution at a concentration of about 0.04% to about 0.0005%, or at a concentration of about 0.002% to about 0.001%. In other embodiments, the sodium channel blocker is in a solution at a concentration of about 0.05% to about 0.0005%, or at a concentration of about 0.05% to about 0.001%.

In some embodiments, the sodium channel blocker is present in a sub-anesthetic concentration. In some embodiments, the sodium channel blocker is present in a sub-toxic concentration. In some embodiments, the sodium channel blocker is present in a therapeutically effective concentration.

In some embodiments, the scleral lens does not touch the cornea of the eye. In some embodiments, the scleral portion of the scleral lens defines at least one channel. In other embodiments, the scleral lens defines at least one fenestration.

In some embodiments, the optic portion of the scleral lens is optically corrective. In other embodiments, the optic portion of the scleral lens is not optically corrective.

In some embodiments, the sodium channel blocker includes a solution of about 0.0009% to about 0.0019% bupivacaine; or a solution of about 0.0014% bupivacaine. In other embodiments, the sodium channel blocker includes a solution of about 0.02% to about 0.001% ropivacaine; or a solution of about 30 µg/mL to about 200 µg/mL ropivacaine.

In some embodiments, the sodium channel modulator includes a solution of about 0.05% to about 0.001% lacosamide; or a solution of about 0.003% lacosamide. In some embodiments, the sodium channel blocker includes a solution of less than or equal to about 0.5% lacosamide; a solution of less than or equal to about 1% lacosamide; a solution of less than or equal to about 5% lacosamide; or a solution of about 0.001% to about 5% lacosamide.

In some embodiments, the sodium channel modulator is lacosamide administered to the eye in the form of eye drops, ointment, gel, or slow release polymer. In some embodiments, the sodium channel modulator includes a solution of less than or equal to about 0.5% lacosamide; a solution of less than or equal to about 1% lacosamide; or a solution of less than or equal to about 5% lacosamide. In some embodiments, the sodium channel modulator includes a solution of about 0.5% to about 1% lacosamide; a solution of less than or equal to about 5% lacosamide; or a solution of about 0.001% to about 5% lacosamide.

In some embodiments, the sodium channel blocker or the sodium channel modulator is administered to the eye, then the scleral lens is applied to the eye. In other embodiments, the sodium channel blocker is added to the scleral lens, then the scleral lens is applied to the eye.

In some embodiments, the patient suffers from corneal neuropathic pain.

DETAILED DESCRIPTION

Figure 1:
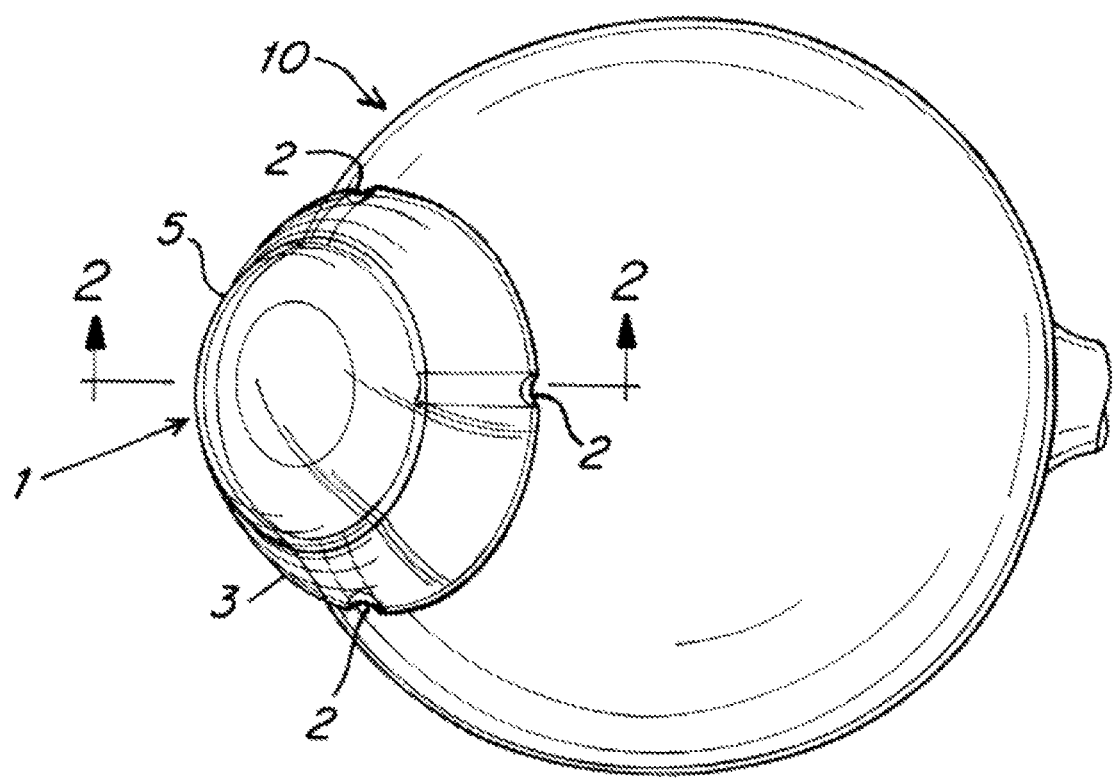
FIG. 1 is a perspective view of an eye with a scleral lens with scalloped channels.

The present disclosure relates to a discovery that sub-anesthetic concentrations of a sodium channel blocker or a sodium channel modulator may treat corneal neuropathic pain when delivered to the eye using a scleral lens. In some embodiments, the sodium channel blocker is a sodium channel blocker anesthetic. These sub-anesthetic concentrations of sodium channel blocker are also sub-toxic, and therefore allow for continued use of the sodium channel blocker in the eye. Without being bound by any particular theory, it is believed that the scleral lens improves retention of the sodium channel blocker or the sodium channel modulator at the surface of the eye, thereby improving the bioavailability of the sodium channel blocker or the sodium channel modulator.

The present disclosure provides a sodium channel blocker delivery system including a scleral lens and a sodium channel blocker (or a sodium channel modulator) disposed on the posterior side of the scleral lens. The sodium channel blocker (or sodium channel modulator) is retained in the expanded pre-corneal tear film defined as the area between the scleral lens and the cornea (i.e., the fluid compartment).

The present disclosure also provides a method of increasing the bioavailability of a sodium channel blocker or a sodium channel modulator delivered to the surface of the eye using a scleral lens, whereby a solution of a sodium channel blocker or a sodium channel modulator is added to the fluid compartment.

The present disclosure also provides a method of retaining a sodium channel blocker or a sodium channel modulator at the surface of the eye using a scleral lens, whereby a solution of a sodium channel blocker or a sodium channel modulator is added to the fluid compartment.

1. Scleral Lens

A scleral lens is described in U.S. Pat. No. 7,591,566, which is incorporated herein by reference in its entirety. A scleral lens is also described in U.S. Pat. No. 7,695,135, which is incorporated herein by reference in its entirety. A method of making a scleral lens is described in U.S. Pat. No. 5,452,031, which is incorporated herein by reference in its entirety.

A scleral lens is a rigid, gas permeable contact lens that rests on the sclera of the eye; some scleral contact lenses rest on the peripheral surface of the cornea while others do not touch the cornea at all. The scleral lens defines a compartment of fluid between the inner surface of the scleral lens and the cornea, referred to herein as the "fluid compartment." The portion of the scleral lens that contacts the sclera is referred to as the "scleral portion" of the scleral lens, or as the "haptic." The portion of the scleral lens that covers the cornea is called the "optic portion" of the scleral lens. The optic portion may optionally be corrective. The greatest distance between the surface of the cornea and the posterior side of the optic portion is at least about 30 microns. As used herein, the posterior side of the scleral lens is the side that is disposed on the eye.

Figure 2:
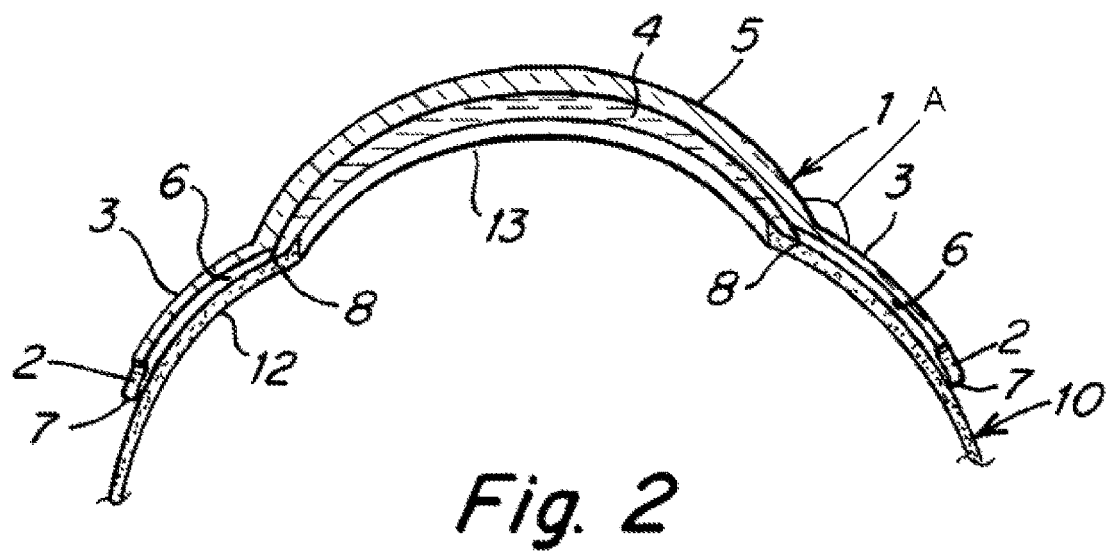
FIG. 2 is a cross-sectional view taken along line 2-2 of FIG. 1.

Referring to FIGS. 1 and 2, the eye has an anterior portion 10. As shown in FIG. 2, the anterior portion 10 of the eye has a sclera 12 and a cornea 13. The sclera 12 is the white part of the eye.

Referring to FIGS. 1 and 2, a scleral lens 1 rests on the anterior portion 10 of an eye. Scleral lens 1 is a rigid lens that rests on the sclera 12 of the eye but either does not touch the cornea 13 or just touches a peripheral surface of cornea 13. The eye and scleral lens 1 define a fluid compartment 4 between the inner surface of the scleral lens and the cornea 13.

The portion of the scleral lens 1 that touches the sclera 12 is referred to as the scleral portion 3 of the scleral lens, or as the "haptic." The portion of the scleral lens 1 that covers the cornea 13 is referred to here as the optic portion 5 of the scleral lens. The optic portion 5 may optionally be corrective. The greatest distance between the surface of the cornea 13 and the posterior side of the optic portion is typically at least 30 microns. As used herein, the posterior side of the scleral lens 1 is the side that is disposed on the eye. The anterior side of the scleral lens 1 is the side facing away from the eye when the scleral lens is disposed on the eye.

As shown in FIG. 2, the curvature of scleral portion 3 is not the same as the curvature of optic portion 5. This difference in curvature causes the optic portion 5 to protrude away from the anterior portion 10 of the eye when disposed on the eye, while the scleral portion 3 conforms to the curvature of the sclera 12, as shown in FIG. 2. The curvature of the optic portion 5 is referred to herein as the first curvature. The curvature of the scleral portion 3 is referred to herein as the second curvature.

The first and second curvatures may be portions of spheres with constant radii. Alternatively, the first and second curvatures are not portions of spheres, so that the first and second curvatures do not have constant radii. Alternatively, the first and second curvatures are adapted based on the topography of the cornea or the sclera of an eye. Scleral lenses with curvatures that do not have constant radii, or that are adapted based on the topography of the cornea or the sclera of an eye, are described at column 4, line 30 through column 9, line 22 in U.S. Pat. No. 5,452,031, the entirety of which patent is incorporated herein by reference.

FIG. 2 shows that the intersection of the optic portion 5 and the scleral portion 3 forms an angle, angle A. Angle A may be uniform throughout the intersection of the optic portion 5 and the scleral portion 3. Alternatively, angle A may vary throughout the intersection of the optic portion 5 and the scleral portion 3. Angle A is less than 180 degrees.

In some embodiments, the posterior side of the scleral portion 3 optionally defines one or more channels 6 that extend generally radially from an outside rim 7 of the scleral lens to an inner rim 8 of the scleral portion. These optional channels are shown in FIGS. 1 and 2. In some embodiments, as shown in FIG. 1, the edge of the channel 6 optionally defines a scallop 2 where the channel 6 meets the outside rim 7 of the scleral lens 1.

In some embodiments, the scleral lens optionally defines one or more fenestrations. As used herein, the term fenestration refers to an opening defined by the scleral lens that allows for fluid and/or gaseous communication between the fluid compartment 4 and the outside of the scleral lens. In another embodiment, the optic portion of the scleral lens defines a circumferential fenestrated channel. A non-limiting example of such a scleral lens is described in U.S. Pat. No. 7,695,135, which is incorporated herein by reference in its entirety.

Another non-limiting example of a scleral lens suitable for use with the present sodium channel blocker delivery system is the Boston Ocular Surface Prosthesis (BOS-P) (Boston Foundation for Sight, Needham, Mass.).

2. Sodium Channel Blockers

Corneal neuropathic pain is associated with abnormal activity of the pain sensors/generators located on the surface of the cornea below the tear/mucin layer. The sensory nerve endings that identify noxious stimulus and convert it into an electrical pain signal are called nociceptors.

Sodium channel blockers, such as local sodium channel blocker anesthetics, function by blocking a key step in the transduction of noxious stimulation into electrical activity: the opening of sodium ion channels in the membrane of nociceptors. The resulting inflow of positively charged sodium ions creates an electrical current which if adequate, results in the generation of action potentials that are conducted to the central nervous system where it is perceived as pain. Sodium channel blockers inactivate sodium ion channels, thereby blocking the transduction of noxious stimulus into a pain signal.

Sodium channel blockers may be used to treat pain throughout the body and have been administered by various routes, including topical delivery. Although sodium channel blockers can be administered by the ocular route, sodium channel blockers can be toxic to the cornea and chronic use can cause permanent corneal damage. Risco and Millar, *Ophthalmology* 99(4):628-633 (1992); Varga et al., *Cornea* 16(4):424-429 (1997), both of which are incorporated herein by reference in their entirety. Accordingly, sodium channel blockers are typically administered to the eye only for diagnostic or short surgical procedures.

Bupivacaine is a sodium channel blocker that may be administered to the eye for limited periods of time. Bupivacaine is used as a topical corneal anesthetic at concentrations of about 0.5% to about 0.75%. A 1 mg dose of bupivacaine, formulated as eye drops and in a soluble hyaluronic acid ophthalmic insert, was also used as an anesthetic during cataract surgery. Mahé et al., *Br. J. Clin. Pharmacol.* 59(2):200-226 (2005), which is incorporated herein by reference in its entirety. Proparacaine at a 0.05% concentration has been used to reduce pain after photorefractive keratectomy. Shahinian et al., *Ophthalmology* 104 (8):1327-1332 (1991), which is incorporated herein by reference in its entirety. This dosage was found to be non-anesthetic, non-toxic, and safe for at least one week of use.

Non-limiting examples of sodium channel blockers suitable for use with the present sodium channel blocker delivery system include tricyclic antidepressants, bupivacaine, lidocaine, proparacaine, tetracaine, ropivacaine, levobupivacaine, flecainide, carbamazepine, and amitriptyline.

As used herein, the phrase "therapeutic effect" is a desired consequence of a medical treatment. As used herein, the phrases "therapeutically effective dose," "therapeutically effective amount," and "therapeutically effective concentration" refer to the dose required to achieve a therapeutic effect. "Therapeutically effective dose," "therapeutically effective amount," and "therapeutically effective concentration" may be used interchangeably.

As used herein, the phrases "anesthetic dose" and "anesthetic concentration" refer to a dose of a sodium channel blocker anesthetic that is sufficient to achieve an anesthetic effect. "Anesthetic dose" and "anesthetic concentration" may be used interchangeably. The anesthetic dose of bupivacaine is 0.5% to 0.75% when formulated for use as eye drops alone (i.e., when not formulated for use in the present sodium channel blocker delivery system). As used herein, an "anesthetic effect" is the elimination of sensation.

As used herein, the phrase "sub-hypoesthetic dose" refers to a dose of a sodium channel blocker or a sodium channel modulator that does not depress corneal sensation. The sub-hypoesthetic dose for a sodium channel blocker or a sodium channel modulator may vary between patients. The sub-hypoesthetic dose of a sodium channel blocker or a sodium channel modulator may vary between patients. The sub-hypoesthetic dose of a sodium channel blocker or a sodium channel modulator can be determined for an individual patient by selecting a higher starting concentration and gradually reducing the concentration via titration until reaching a sub-hypoesthetic dose as determined by a contact and non-contact esthesiometer. A non-limiting example of a method of determining corneal sensitivity is Cochet-Bonnet aesthesiometry.

As used herein, the phrases "sub-anesthetic dose" and "sub-anesthetic concentration" refer to a dose of a sodium channel blocker or a sodium channel modulator or a sodium channel modulator that is lower than the anesthetic dose. "Sub-anesthetic dose" and "sub-anesthetic concentration" may be used interchangeably. The sub-anesthetic dose of a sodium channel blocker or a sodium channel modulator may vary between patients. The sub-anesthetic dose of a sodium channel blocker or a sodium channel modulator can be determined for an individual patient by selecting a higher starting concentration and gradually reducing the concentration via titration until reaching a sub-anesthetic dose as determined by a contact and non-contact esthesiometer. A non-limiting example of a starting concentration of a sodium channel blocker or a sodium channel modulator is about 0.02%. In some embodiments, the concentration of the sodium channel blocker or a sodium channel modulator may be titrated down to a concentration that avoids any depression of corneal sensitivity. A non-limiting example of a method of determining corneal sensitivity is Cochet-Bonnet aesthesiometry.

As used herein, the phrases "toxic concentration," "toxic dose," and "toxic amount" refer to a dose of a compound that causes cellular damage to the tissue to which it is applied. The phrases "toxic concentration," "toxic dose," and "toxic amount" also refer to a dose that causes unwanted side effects. The phrases "toxic concentration," "toxic dose," and "toxic amount" may be used interchangeably.

The phrases "sub-toxic concentration," "sub-toxic dose," and "sub-toxic amount" refer to a dose of a compound that does not cause cellular damage to the tissue to which it is applied, or that does not cause unwanted side effects. The phrases "sub-toxic concentration," "sub-toxic dose," and "sub-toxic amount" may be used interchangeably.

3. Scleral Lens/Sodium Channel Blocker Combination; Scleral Lens/Sodium Channel Modulator Combination A scleral lens can be used as a sodium channel blocker delivery system (or as a sodium channel modulator) by providing a sodium channel blocker or a sodium channel modulator in the fluid compartment, thus keeping the sodium channel blocker or sodium channel modulator in contact with the surface of the cornea. The scleral lens/sodium channel blocker combination is referred to herein as the "sodium channel blocker delivery system." The scleral lens/sodium channel modulator combination is referred to herein as the "sodium channel modulator delivery system." The sodium channel blocker delivery system (or sodium channel modulator delivery system) may be used in a method of treating corneal neuropathic pain, where the sodium channel blocker delivery system (or sodium channel modulator delivery system) is applied to the eye of a patient. The sodium channel blocker delivery system (or sodium channel modulator delivery system) may be used in a method of retaining a sodium channel blocker (or sodium channel modulator) at the surface of an eye of a patient, where the sodium channel blocker delivery system (or sodium channel modulator delivery system) is applied to the eye of a patient.

In some embodiments, a solution of the sodium channel blocker or the sodium channel modulator is added to the posterior side of the scleral lens, then the scleral lens is applied to the patient's eye. In other embodiments, a solution of the sodium channel blocker or the sodium channel modulator is administered to the patient's eye, then the scleral lens is applied to the patient's eye.

Surprisingly, sub-anesthetic concentrations of sodium channel blocker (or sodium channel modulator) may be used in the present sodium channel blocker delivery system (or sodium channel modulator delivery system) to produce a therapeutic effect, e.g., to treat corneal neuropathic pain. Furthermore, the combination of a sub-anesthetic concentration of a sodium channel blocker (or sodium channel modulator) with a scleral lens can produce a therapeutic effect, e.g., treat corneal neuropathic pain, while retaining the treated eye's normal sense of touch.

Solutions containing about 0.04% to about 0.0005% of a sodium channel blocker or sodium channel modulator may be used with the sodium channel blocker delivery system (or sodium channel modulator delivery system) of the present disclosure. Alternatively, the sodium channel blocker delivery system (or sodium channel modulator delivery system) includes a solution containing about 0.002% to about 0.001% of a sodium channel blocker (or sodium channel modulator). In some embodiments, the sodium channel blocker delivery system includes a solution containing about 0.0001% to about 0.05% of a sodium channel blocker. In some embodiments, the sodium channel modulator delivery system includes a solution containing about 0.001% to about 0.5% of a sodium channel modulator. In some embodiments, the sodium channel blocker delivery system (or sodium channel modulator delivery system) includes a solution containing about 0.0019% to about 0.0009% of a sodium channel blocker (or sodium channel modulator). In still other embodiments, the sodium channel blocker delivery system (or sodium channel modulator delivery system) includes a solution containing about 0.0014% of a sodium channel blocker (or sodium channel modulator). In other embodiments, the sodium channel blocker delivery system (or sodium channel modulator delivery system) includes a solution containing about 0.02% to about 0.0025% of a sodium channel blocker (or sodium channel modulator).

In some embodiments, only one sodium channel blocker (or sodium channel modulator) is used in the sodium channel blocker delivery system (or sodium channel modulator delivery system) of the present disclosure. In other embodiments, combinations of more than one sodium channel blocker (or sodium channel modulators) are used in the sodium channel blocker delivery system of the present disclosure. In some embodiments, combinations of two, three, four, five, six, seven, eight, nine, or ten different sodium channel blockers (or sodium channel modulators) are used in the sodium channel blocker delivery system of the present disclosure.

In one embodiment, the sodium channel blocker includes a solution of about 0.0014% to about 0.001% bupivacaine. In another embodiment, the sodium channel blocker includes a solution of about 0.0009% to about 0.0019% bupivacaine. In another embodiment, the sodium channel blocker includes a solution of about 0.02% to about 0.0025% ropivacaine. In another embodiment, the sodium channel blocker includes a solution of about 30 μg/mL to about 200 μg/mL ropivacaine.

In another embodiment, the sodium channel blocker includes a solution containing about 0.0005%, about 0.001%, about 0.0015%, about 0.002%, about 0.0025%, about 0.003%, about 0.0035%, about 0.004%, about 0.0045%, about 0.005%, about 0.0055%, about 0.006%, about 0.0065%, about 0.007%, about 0.0075%, about 0.008%, about 0.0085%, about 0.009%, about 0.0095%, about 0.01%, about 0.02%, about 0.03%, about 0.04%, or about 0.05% of a sodium channel blocker.

The sodium channel blocker delivery system (or sodium channel modulator delivery system) disclosed herein can provide relief from corneal neuropathic pain within about 30 minutes of applying the sodium channel blocker delivery system (or sodium channel modulator delivery system) to an eye. In certain instances, the sodium channel blocker delivery system (or sodium channel modulator delivery system) may be used for a period of time ranging from one day to every day for one year. In other instances, the sodium channel blocker delivery system (or sodium channel modulator delivery system) may be used every day for more than one year. In some instances, the sodium channel blocker delivery system (or sodium channel modulator delivery system) may be worn for a period of time ranging from about one hour per day to all waking hours of the day. In a non-limiting example, the sodium channel blocker delivery system (or sodium channel modulator delivery system) may be worn all waking hours of the day, every day for a year or longer.

Solutions containing a sodium channel blocker (or sodium channel modulator) for use in the present sodium channel blocker delivery system (or sodium channel modulator delivery system) are formulated to be suitable for ocular use. A non-limiting example of such a solution is a solution including normal saline and a sodium channel blocker (or sodium channel modulator).

Non-limiting examples of diseases or conditions that may be treated using the sodium channel blocker delivery system (or sodium channel modulator delivery system) of the present disclosure include corneal neuropathic pain caused by cosmetic lid surgery, Lasik surgery, Sjögren's syndrome and other autoimmune disorders, dry eye, exposure to noxious fumes, exposure to ultraviolet B, and exposure to ACCUTAINE® (isotretinoin). The terms "disease," "condition," and "disorder" are used interchangeably herein.

Additional pharmaceutically acceptable compounds or excipients known to those of ordinary skill in the art may optionally be used with the sodium channel blocker delivery system (or sodium channel modulator delivery system) of the present disclosure. For example, compounds that increase the absorption of a sodium channel blocker (or sodium channel modulator) by the cornea may be used. Non-limiting examples of compounds that increase the absorption of a sodium channel blocker (or sodium channel modulator) by the cornea include dimethyl sulfoxide (DMSO).

The sodium channel blocker delivery system (or sodium channel modulator delivery system) of the present disclosure may also be used without any additional pharmaceutically acceptable compounds or excipients.

4. Sodium Channel Modulators

The instant disclosure also relates to a sodium channel modulator delivery system. Sodium channel modulators are compounds that enhance slow inactivation of voltage gated sodium channels. A non-limiting example of a sodium channel modulator is lacosamide. Lacosamide is a novel sodium channel modulator developed for the management of epileptic seizures and diabetic neuropathy.

Lacosamide enhances slow inactivation of the sodium ion channel blockers in the sensory nerve terminals (nociceptors), a process that occurs over hundreds of milliseconds or longer. Recovery can take as long. This is different than local anesthetics in which the mechanism of action is prolonging fast inactivation. The mechanism of local anesthetics is based on their ability to delay the recovery of nociceptors from fast inactivation. It is estimated that lacosamide inactivates voltage gated sodium channels for a period of time 100 to 1,000 fold greater than local anesthetics. (Errington et al., *Mol. Pharmacol.* 73(1):157-69 (2008), which is incorporated herein by reference in its entirety). Therefore, lacosamide can provide a longer duration of action than other sodium channel blockers.

Slow inactivation occurs preferentially in tonically active nociceptors and is facilitated by prolonged depolarization. Presumably, this phenomenon is a physiological mechanism for dampening the hyperactivity of sensitized nociceptors. Theoretically, a drug that facilitates the entry of hyperactive, sensitized nociceptors into the slow inactivation state may be effective in down-regulating preferentially abnormal nociceptive activity responsible for corneal hyperalgesia and pain while preserving the function of mechanoreceptors and normally functioning nociceptors. Another advantage of a drug that enhances slow but not fast inactivation is that it not blocking sodium channels, it does not have local anesthetic properties. Lacosamide has these properties.

Lacosamide has a selective effect on dysfunctional, hyperactive voltage gated sodium channels (e.g., it acts only on depolarized neurons and those that have been active for some time) (Sheets et al., *J. Pharmacol. Exp. Ther.* 326(1): 89-99 (2008), which is incorporated herein by reference in its entirety). Lacosamide is especially effective in targeting sodium channels involved in sustained high frequency neuronal firing or those affected by prolonged depolarization. These are typical characteristics of the dysfunctional voltage-gated sodium channels responsible for neuropathic pain. Moreover, slow inactivation can be expected to have less anesthetic effect because it does not completely block the sodium ion channels.

Without being bound to any particular theory, it is believed that the effectiveness of sodium channel modulators in treating corneal neuropathic pain is due to their ability to target hyperactive nociceptors and ectopic firing sites without affecting normal corneal sensitivity.

Lacosamide is water soluble and can be delivered to the corneal surface in the form of eye drops (i.e., ophthalmic solutions). Other non-limiting examples of lacosamide formulations suitable for use in the present disclosure include ophthalmic suspensions and ophthalmic ointments. Non-limiting examples of how to make and use eye drops, ophthalmic suspensions, ophthalmic ointments, and other ophthalmic preparations may be found in such standard references as Gerald Hecht, *Chapter 43: Ophthalmic Preparations*, in REMINGTON: THE SCIENCE AND PRACTICE OF PHARMACY, 821-835 (A. R. Gennaro, ed., 20th edition, Lippincott Williams & Wilkins, Philadelphia, Pa., 2000), which is incorporated herein by reference in its entirety.

Lacosamide may be embedded in a slow release polymer which is then positioned under an eyelid, or which is used to form a contact lens. A non-limiting example of a slow release polymer suitable for use with the present disclosure is nanofiber hydrogel scaffolding. Lacosamide may also be delivered to the corneal surface using the sodium channel modulator delivery system described herein.

In some embodiments, lacosamide is the only drug used in the sodium channel modulator delivery system of the present disclosure. In other embodiments, lacosamide is used in combination with other drugs in the sodium channel modulator delivery system (or sodium channel blocker delivery system) of the present disclosure. In still other embodiments, lacosamide is used in combination with at least one sodium channel blocker in the sodium channel blocker delivery system of the present disclosure. In yet other embodiments, lacosamide is used in combination with one, two, three, four, five, six, seven, eight, nine, or ten sodium channel blockers in the sodium channel modulator delivery system (or sodium channel blocker delivery system) of the present disclosure.

Solutions containing less than or equal to about 5% lacosamide (including but not limited to about 0.0001% to about 0.05% lacosamide; about 0.0001% to about 5.0% lacosamide; about 0.05% to about 1.0% lacosamide; about 0.001% to about 0.05% lacosamide; about 0.001% to about 5% lacosamide; about 0.5% lacosamide to about 1% lacosamide; about 0.5% lacosamide; about 0.05% lacosamide; or about 5% lacosamide) may be used in the sodium channel modulator delivery system (or sodium channel blocker delivery system) described herein. Lacosamide may be used at concentrations of less than about 5% (including but not limited to about 0.001% to about 0.05% lacosamide; about 0.001% to about 5% lacosamide; about 0.5% lacosamide; about 1% lacosamide; about 0.5% lacosamide; about 0.05% lacosamide; or about 5% lacosamide) when it is not used in the sodium channel modulator delivery system (or sodium channel blocker delivery system) (i.e., when lacosamide is delivered in eye drops, gels, ointments, etc. without using a scleral lens).

In one embodiment, the sodium channel modulator includes a solution containing about 0.001%, about 0.0015%, about 0.002%, about 0.0025%, about 0.003%, about 0.0035%, about 0.004%, about 0.0045%, about 0.005%, about 0.0055%, about 0.006%, about 0.0065%, about 0.007%, about 0.0075%, about 0.008%, about 0.0085%, about 0.009%, about 0.0095%, about 0.01%, about 0.02%, about 0.03%, about 0.04%, about 0.05%, about 0.06%, about 0.07%, about 0.08%, about 0.09%, about 1.0%, about 1.5%, about 2.0%, about 2.5%, about 3.0%, about 3.5%, about 4.0%, about 4.5%, or about 5.0% lacosamide.

5. Combinations

In some embodiments, the sodium channel blocker (or sodium channel modulator) includes a combination of lacosamide and at least one other sodium channel blocker. Non-limiting examples of combinations of sodium channel blockers (or sodium channel modulators) include lacosamide and bupivacaine, lacosamide and lidocaine, lacosamide and proparacaine, lacosamide and flecainide, lacosamide and tetracaine, lacosamide and ropivacaine, lacosamide and levobupivacaine, lacosamide and flecainide, lacosamide and carbamazepine, and lacosamide and amitriptyline. In some embodiments, the total combined amount of sodium channel blockers (or sodium channel modulators) in the solution is about 0.0005%, about 0.001%, about 0.0015%, about 0.002%, about 0.0025%, about 0.003%, about 0.0035%, about 0.004%, about 0.0045%, about 0.005%, about 0.0055%, about 0.006%, about 0.0065%, about 0.007%, about 0.0075%, about 0.008%, about 0.0085%, about 0.009%, about 0.0095%, about 0.01%, about 0.02%, about 0.03%, about 0.04%, or about 0.05% of a sodium channel blocker (or sodium channel modulator). In some embodiments, the total combined amount of sodium channel blockers (or sodium channel modulators) in the solution is about 0.04% to about 0.0005%, about 0.002% to about 0.001%, about 0.0019% to about 0.0009%, or about 0.02% to about 0.0025%. In some embodiments, the sodium channel blocker delivery system (or sodium channel modulator delivery system) includes a solution containing about 0.0001% to about 0.05% of a sodium channel blocker and about 0.001% to about 0.5% of a sodium channel modulator.

In other embodiments, the method includes alternating between lacosamide and at least one other sodium channel blocker (or sodium channel modulator) at an alternation interval. The alternation interval is the amount of time over which each sodium channel blocker (or sodium channel modulator) is used for treatment before switching to a different sodium channel blocker (or sodium channel modulator). In one embodiment, the alternation interval is one day, i.e., the patient is treated with lacosamide for one day, then with a different sodium channel blocker (or sodium channel modulator) for one day, then with lacosamide for one day, then with the different sodium channel blocker (or sodium channel modulator) for one day, and so on for the duration of treatment. In other embodiments, the alternation interval is two days, three days, four days, five days, six days, seven days, eight days, nine days, ten days, eleven days, twelve days, thirteen days, or fourteen days.

As will be apparent to one of ordinary skill in the art from a reading of this disclosure, the embodiments of the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

Example 1

A patient with well-established primary Sjögren's syndrome and severe dry eyes was treated for intense, constant corneal pain using the anesthetic delivery system disclosed herein. Specifically, the patient was treated with bupivacaine and BOS-P devices. The concentration of non-preserved bupivacaine was rapidly titrated using frequent (every 2-5 minutes) drops in the more symptomatic left eye (open label) measuring corneal sensitivity with a Cochet-Bonnet aesthesiometer (with adequate recovery times) until reaching the concentration that avoided any depression of corneal sensitivity. The sub-anesthetic concentration in this patient was determined to be 0.001%. Both BOS-P devices were filled with 0.001% bupivacaine and inserted into the patient's eyes. The patient then left.

The patient returned the next day volunteering that both eyes felt more comfortable than they had been in 3 months. After verifying the non-anesthetic effect of the 0.001% bupivacaine concentration using sequential drops in her left eye, the reservoir of the left lens was filled with non-preserved bupivacaine, and the absence of depressed corneal sensitivity was periodically verified during the day. At day's end, the patient reported the virtual absence of pain in either eye. The patient reported little or no pain after exposure to glass cleaner or a white board marker in the examining room, which would ordinarily trigger severe pain. The patient was given a vial of 0.01% bupivacaine to dilute 1:10 (e.g., add one drop of 0.01% bupivacaine to nine drops of saline) to fill the reservoir of the left lens prior to inserting it the next morning.

The next day, the patient reported virtually no pain in either eye with the Visual Analog Scale. She wore the BOS-P containing 0.001% bupivacaine in her left eye, and the BOS-P containing saline in her right eye unmasked to the patient and doctor, for about 8 hours. At that time she again reported virtually no pain in either eye, even though the right eye was not treated with bupivacaine. The lenses were removed and there was no significant fluorescein staining in either eye. Corneal sensation in the treated eye was normal.

Example 2

After upper and lower cosmetic lid surgery in both eyes, a patient suffered from corneal exposure and desiccation of her corneas associated with severe chronic eye pain and disabling photosensitivity that persisted after her corneas healed. Symptoms were somewhat lessened after she was fitted with a BOS-P scleral lens for each eye, but remained sufficiently severe so that she was unable to read for more than 1-2 minutes.

The fluid compartments of both BOS-P lenses were filled with non-preserved bupivacaine at a concentration of 0.002%, and the BOS-P lenses with bupivacaine were worn at least 12 hours/day. Over several weeks, all eye symptoms (e.g., photosensitivity, burning pain, inability to read) resolved while corneal sensation remained intact as documented by Cochet-Bonnet aesthesiometry. Eye symptoms were also resolved after the bupivacaine was diluted to 0.0014%.

Example 3

A patient suffered from Stevens-Johnson syndrome for about 25 years, complicated by scarring of the lids and corneas of both eyes. The patient was fitted with scleral lens with marked mitigation of eye pain for 2 years following which the patient experienced increasingly disabling eye pain and photosensitivity that was refractory to all available treatments and required high daily doses of opioids to control. Three drops of ropivacaine 0.04% were mixed with 5 drops of saline in the reservoirs of both of the patient's scleral lenses, yielding a solution of 0.015% ropivacaine. Following application of the scleral lenses containing ropivacaine to the patient's eyes, the patient reported a rapid mitigation of eye pain and photosensitivity.

The patient returned the following day 2 hours after inserting the scleral lenses containing 0.015% ropivacaine. The patient reported having worn the lenses until midnight the previous day with total resolution of eye pain and photophobia. The patient was free of symptoms at the time of examination. The patient's eyes showed no adverse effects from the treatment, and corneal sensitivity was normal as measured by the Cochet-Bonnet aesthesiometer. The patient continued to report significant mitigation of eye pain and photophobia and normal corneal sensitivities without adverse treatment-related complications at subsequent examinations.

Example 4

A patient suffered from severe corneal neuropathic pain for many years, greatly limiting the patient's quality of life. This disease was refractory to previous treatments. Lacosamide was placed in the fluid reservoir of the device where it remained in contact with the cornea while it was worn (approximately 10 hours/day). Titration indicated that the maximum concentration that avoided significant depression of corneal sensation was 0.003% and this concentration was used in the fluid reservoir of the BOS-P. This significantly mitigated the patient's corneal neuropathic pain without any detrimental effects to the corneas, as determined by slit lamp examination and confocal microscopy.

Example 5

Eye drops containing 0.5% lacosamide were administered to the eyes of two patients and to the an eye of the inventor. The 0.5% lacosamide solution did not depress corneal sensation in any eye to which the 0.5% lacosamide solution was administered. The 0.5% lacosamide solution provided complete resolution of corneal neuropathic pain in both patients almost immediately after administration. The effect lasted over four hours in one patient and over two hours in the other patient. Therefore, it is believed that lacosamide may be used in eye drops at a concentration of up to 5% to treat corneal neuropathic pain without depressing corneal sensation.

Example 6

A 39 year old patient underwent a bone marrow stem cell transplant for leukemia and subsequently developed severe dry eyes secondary to chronic graft versus host disease. She was fitted with a scleral lens that eliminated the severe burning pain in her right eye but continued to experienced knife-like and severe aching pain in her left eye and disabling photosensitivity while wearing the scleral lens. This persisted for 15 months. All eye and co-morbid pain symptoms disappeared when the lens was worn with its fluid reservoir filled with sterile, non-preserved lacosamide 0.05%.

The invention claimed is:
1. A method of treating corneal neuropathic pain in the eye of a patient, the method comprising:
applying to the eye of a patient suffering from corneal neuropathic pain, a sodium channel modulator delivery system adapted for treatment of corneal neuropathic pain comprising:
(a) a scleral lens to be disposed on an eye of a patient, the scleral lens comprising:
an optic portion having a first curvature, and a scleral portion having a second curvature, wherein:
(i) the first curvature is adapted to cover a cornea of the eye creating a reservoir between the first curvature and the cornea without any contact between the first curvature and the cornea, and
(ii) the second curvature is adapted to align with the shape of a sclera of the eye, on which the second curvature rests; and
alternating the administration of a solution comprising lacosamide with the administration of a solution comprising at least one of bupivacaine, lidocaine, proparacaine, flecainide, tetracaine, ropivacaine, levobupivacaine, carbamazepine, and amitriptyline at an alternation interval.
2. The method of claim 1, wherein the alteration is about one day to about fourteen days.

3. A method of increasing the bioavailability of a sodium channel modulator at the eye of a person, the method comprising the steps of applying a solution comprising lacosamide to the eye of a person;

applying a scleral lens on the eye of the patient, such that an optic portion of the lens having a first curvature covers a cornea of the eye and creates a reservoir for the solution between the first curvature and the cornea without any contact between the first curvature and the cornea and a scleral portion of the lens having a second curvature aligns with the shape of a sclera of the eye, on which the second curvature rests.

4. The method of claim 3, wherein the solution comprising lacosamide is administered to the eye, then the scleral lens is applied to the eye.

5. The method of claim 3, wherein the solution comprising lacosamide is added to the scleral lens, then the scleral lens is applied to the eye.

6. The method of claim 3, wherein the lacosamide is in the solution at a concentration of less than or equal to about 5% lacosamide.

7. The method of claim 3, wherein the lacosamide is in the solution at a concentration of about 0.001% to about 5.0% lacosamide.

8. The method of claim 3, wherein the lacosamide is in the solution at a concentration of about 0.5% to about 1.0% lacosamide.

9. The method of claim 3, wherein the lacosamide is in the solution at a concentration of about 0.5% lacosamide.

10. The method of claim 3, wherein the lacosamide is in the solution at a concentration of about 1.0% lacosamide.

11. The method of claim 3, wherein the lacosamide is in the solution at a concentration of about 0.003% lacosamide.

12. The method of claim 3, further comprising alternating the administration of the solution comprising lacosamide with the administration of a solution comprising at least one of bupivacaine, lidocaine, proparacaine, flecainide, tetracaine, ropivacaine, levobupivacaine, carbamazepine, and amitriptyline at an alternation interval.

13. The method of claim 12, wherein the alternation interval is about one day to about fourteen days.

14. A sodium channel modulator delivery system for increasing the bioavailability of a sodium channel modulator at the eye of a person comprising:

(a) a scleral lens to be disposed on an eye of a patient, the scleral lens comprising:

an optic portion having a first curvature, and a scleral portion having a second curvature, wherein:

(i) the first curvature is configured to cover a cornea of the eye to create a reservoir between the scleral lens and the cornea without any contact between the scleral lens and the cornea, and (ii) the second curvature is shaped to rest on a sclera of the eye; and (b) a solution comprising lacosamide disposed in the reservoir between the first curvature and the cornea.

15. The sodium channel modulator delivery system of claim 14, wherein the lacosamide is in the solution at a concentration of less than or equal to about 5% lacosamide.

16. The sodium channel modulator delivery system of claim 14, wherein the lacosamide is in the solution at a concentration of about 0.001% to about 5.0% lacosamide.

17. The sodium channel modulator delivery system of claim 14, wherein the lacosamide is in the solution at a concentration of about 0.5% to about 1.0% lacosamide.

18. The sodium channel modulator delivery system of claim 14, wherein the lacosamide is in the solution at a concentration of about 0.5% lacosamide.

19. The sodium channel modulator delivery system of claim 14, wherein the lacosamide is in the solution at a concentration of about 1.0% lacosamide.

20. The sodium channel modulator delivery system of claim 14, wherein the lacosamide is in the solution at a concentration of about 0.003% lacosamide.

\* \* \* \* \*